(12) United States Patent
Cutting (10) Patent No.: US 8,550,703 B2
(45) Date of Patent: Oct. 8, 2013

(54) SYSTEMS AND METHODS FOR USE IN FREEZING OR THAWING BIOPHARMACEUTICAL MATERIALS

(75) Inventor: Jonathan Cutting, Fairfield, CA (US)

(73) Assignee: Sartorius Stedim North America Inc., Bohemia, NY (US)

(*) Notice: Subject to any disclaimer, the term of this patent is extended or adjusted under 35 U.S.C. 154(b) by 335 days.

(21) Appl. No.: 12/891,213

(22) Filed: Sep. 27, 2010

(65) Prior Publication Data

US 2012/0073312 A1   Mar. 29, 2012

(51) Int. Cl.
*G01N 25/00*  (2006.01)
*G01K 11/00*  (2006.01)
*G01K 1/00*   (2006.01)

(52) U.S. Cl.
USPC ................ 374/16; 374/117; 374/208

(58) Field of Classification Search
USPC .......................... 374/16, 117, 208
See application file for complete search history.

(56) References Cited

U.S. PATENT DOCUMENTS

| | | | |
|---|---|---|---|
| 3,832,887 A | 9/1974 | Zeutschel | |
| 3,986,385 A | 10/1976 | Johnston et al. | |
| 4,452,090 A | 6/1984 | Kou et al. | |
| 4,527,420 A | 7/1985 | Foote | |
| 5,009,102 A * | 4/1991 | Afromowitz | 73/590 |
| 5,507,178 A * | 4/1996 | Dam | 73/61.49 |
| 5,661,233 A | 8/1997 | Spates et al. | |
| 5,731,521 A * | 3/1998 | Lanagan et al. | 73/632 |
| 5,966,966 A | 10/1999 | Botsaris et al. | |
| 6,612,156 B1 * | 9/2003 | Hakimuddin | 73/61.75 |
| 2003/0051535 A1 * | 3/2003 | Coupland et al. | 73/64.53 |
| 2004/0037742 A1 * | 2/2004 | Jen et al. | 422/68.1 |
| 2005/0092058 A1 * | 5/2005 | Ellson et al. | 73/1.82 |
| 2005/0115323 A1 * | 6/2005 | Segura et al. | 73/596 |
| 2006/0191344 A1 * | 8/2006 | Hashimoto | 73/632 |
| 2009/0089008 A1 * | 4/2009 | Stoddard et al. | 702/170 |

FOREIGN PATENT DOCUMENTS

| | | |
|---|---|---|
| EP | 0 577 511 A1 | 1/1994 |
| EP | 0 577 511 B1 | 1/1994 |
| EP | 0 584 127 B1 | 3/1997 |
| EP | 1 303 745 B1 | 6/2006 |

(Continued)

OTHER PUBLICATIONS

Translation of EP 0577511.*

(Continued)

*Primary Examiner* — Mirellys Jagan
(74) *Attorney, Agent, or Firm* — Heslin Rothenberg Farley & Mesiti P.C.; Nicholas Mesiti, Esq.; Victor A. Cardona, Esq.

(57) ABSTRACT

A system for use in freezing or thawing a biopharmaceutical material includes a container means and a support member. The container means has a receiving cavity receiving the biopharmaceutical material therein. The support member is connected to and supported by the container means. A transmitter is configured to propagate an ultrasonic pulse into the biopharmaceutical material and is located in a support member cavity of the support member. An ultrasonic sensor is configured to sense a reflection of the pulse in the biopharmaceutical material and is located in the support member cavity. A controller is coupled to the transmitter and the sensor. The controller is configured to determine a phase change of the biopharmaceutical material based on the propagation of the pulse by the transmitter and the sense of the reflection by the sensor.

24 Claims, 4 Drawing Sheets

(56) References Cited

FOREIGN PATENT DOCUMENTS

| EP | 2 081 022 A1 | 7/2009 |
|---|---|---|
| JP | 60-256049 | 12/1985 |
| JP | 2005-351753 | 12/2005 |
| WO | WO 91/07085 | 5/1991 |
| WO | WO 2007/000047 A1 | 1/2007 |
| WO | WO 2008/090242 A1 | 7/2008 |

OTHER PUBLICATIONS

Laugier P., et al., "Split Spectrum Processing for Enhanced Detection of the Ultrasonic Echo of a Moving Target in Biological Tissues", Ultrasonics Symposium, 1993, Proceedings., IEEE 1993 Baltimore, MD, USA, Oct. 31-Nov. 3, 1993, New York, NY, USA, IEEE, Oct. 31, 1993 pp. 999-1003.

McClements D. Julian, "Ultrasonic Characterization of Foods and Drinks: Principles, Methods and Applications", Critical Reviews in Food Science and Nutrition, Boca Raton, FL, US., vol. 37, No. 1, Jan. 1, 1997, pp. 1-46.

Notification of Transmittal (PCT/ISA/220) of the International Search Report (PCT/ISA8/210) and The Written Opinion (PCT/ISA/237) of the International Searching Authority, or the Declaration, for corresponding International Application No. PCT/US2011/047736 filed on Aug. 15, 2011, dated Nov. 1, 2011 and mailed on Nov. 8, 2011.

Sigfusson et al., "Ultrasonic Monitoring of Food Freezing", Journal of Food Engineering 62 (2004), 263-269.

Aparicio et al., "Ice Content and Temperature Determination from Ultrasonic Measurements in Partially Frozen Foods", Journal of Food Engineering 88 (2008), 272-279.

\* cited by examiner

SYSTEMS AND METHODS FOR USE IN FREEZING OR THAWING BIOPHARMACEUTICAL MATERIALS

TECHNICAL FIELD

This invention relates, in general, to biopharmaceutical materials, preservation methods and systems, and more particularly to systems and methods for freezing, storing, transporting, and thawing biopharmaceutical materials.

BACKGROUND ART

Preservation of biopharmaceutical materials, such as a bulk drug substance (BDS), is important in the manufacture, use, transport, storage and sale of such materials. For example, bulk drug substance is often preserved by freezing during storage. Similarly, bulk drug substance is often frozen and thawed as part of the development process to enhance the quality or to simplify the development process. Bulk drug substance may also need to be stored and shipped at a certain temperature range.

When freezing bulk drug substance, the overall quality, and in particular pharmaceutical activity, of the bulk drug substance is desirably preserved, without substantial degradation of the bulk drug substance. When freezing or thawing an aqueous solution, such as bulk drug substance, temperature sensors (e.g., an RTD in a thermowell) have typically been used to monitor the process. Such a temperature sensor provides useful information at the beginning and end of a freeze or thaw as the solution loses or gains sensible heat. However, the sensor is of little use during the middle of a freeze or thaw, for about half of the process, because the loss or gain of latent heat due to phase change has no accompanying change in temperature. Unless an array of temperature sensors is used, there is no way to know to what extent the material has been frozen or thawed. Thus, it would be advantageous to have a sensor that can determine the extent of phase change in a material being frozen or thawed.

Thus, there is a need for systems and methods for freezing, thawing, and storing biopharmaceutical materials, which allow the monitoring of phase changes in such biopharmaceutical materials during freezing and thawing.

SUMMARY OF THE INVENTION

The present invention provides, in one aspect, a system for use in freezing or thawing biopharmaceutical materials, which includes a container means and a support member. The container means has a receiving cavity for receiving a biopharmaceutical material therein. The support member is connected to and supported by the container means. A transmitter is configured to propagate an ultrasonic pulse into the biopharmaceutical material and is located in a support member cavity of the support member. An ultrasonic sensor is configured to sense a reflection of the pulse in the biopharmaceutical material and is located in the support member cavity. A controller is coupled to the transmitter and the sensor. The controller is configured to determine a phase change of the biopharmaceutical material based on the propagation of the pulse by the transmitter and the sense of the reflection by the sensor.

In another aspect, the transmitter and sensor may consist of a single piezoelectric transducer. A support member may be mounted on a side wall of the container means or on a top wall of the container means. Also, the transmitter may be located such that a pulse is propagated from the transmitter to a solid phase of the biopharmaceutical material parallel to a direction of ice growth of the biopharmaceutical material and the pulse is reflected at a liquid/solid interface of the biopharmaceutical material. Further, the transmitter may be located such that the pulse is propagated from the transmitter through a liquid phase of the biopharmaceutical material perpendicular to a direction of ice growth of the biopharmaceutical material and the pulse is reflected at a liquid/solid interface of the biopharmaceutical material.

In a further aspect, the support member including a sensor well may be mounted on the top wall of the container means. The transmitter may include a probe located in the sensor well such that an end of the probe extends into a portion of the sensor well surrounded by a liquid portion of the biopharmaceutical material.

In yet another aspect, the support member cavity may include an encapsulant substantially filling an empty portion of the support member cavity between the sensor and an interior wall of the support member adjacent the biopharmaceutical material and bounding the support member cavity to acoustically couple the sensor to the biopharmaceutical material. The support member may be fixedly connected to the container means such that an exterior surface of the support member contacts the biopharmaceutical material.

In a further aspect, the support member cavity may be sealed and avoid communication with an area external to the support member cavity. The sensor may be removably received in the support member cavity.

In yet a further aspect, the support member cavity may have an end in communication with an area external to the support member cavity to allow the sensor to be removably inserted into the support member cavity. The support member cavity may receive a coupling agent between the sensor and an interior wall of the support member adjacent the biopharmaceutical material and bounding the support member cavity to acoustically couple the sensor to the biopharmaceutical material.

In another aspect, the support member includes a heater configured to heat the biopharmaceutical material to provide a pathway for a liquid portion of the biopharmaceutical material toward a headspace above the biopharmaceutical material.

The present invention provides, in a further aspect, a method for freezing or thawing biopharmaceutical materials, which includes receiving a biopharmaceutical material in a receiving cavity of a container means. The container means is connected to and supports the support member. A transmitter propagates an ultrasonic pulse into the biopharmaceutical material and the transmitter is located in a support member cavity of the support member. An ultrasonic sensor senses reflection of the pulse in the biopharmaceutical material and the sensor is located in the support member cavity. A controller is coupled to the transmitter and the sensor. The controller determines a phase change in the biopharmaceutical material based on the propagation of the pulse by the transmitter and the sense of the reflection by the sensor.

In yet another aspect, the transmitter and the sensor may consist of a single piezoelectric transducer. Also, the support member may be mounted on a sidewall of the container means or on a top wall of the container means.

In a further aspect, the support member may include a sensor well on a top wall of the container means and a transmitter may include a probe located in the sensor well such that an end of the probe extends into a portion of a sensor well surrounded by a liquid portion of the biopharmaceutical material.

In yet another aspect, an encapsulant may be introduced into the support member cavity to substantially fill an empty portion of the support member cavity between the sensor and an interior wall of the support member adjacent the biopharmaceutical material and bounding the support member cavity to acoustically couple the sensor to the biopharmaceutical material. Also, the support member may be fixedly connected to the container means such that an exterior surface of the support member contacts the biopharmaceutical material.

In a further aspect, communication may be avoided between the support member cavity and an area external to the support member cavity.

In yet a further aspect, the sensor may be removably received in the support member cavity.

In yet another aspect, communication may be provided between an end of the support member cavity and an area external to the support member cavity to allow the sensor to be removably inserted into the support member cavity.

BRIEF DESCRIPTION OF THE DRAWINGS

The subject matter which is regarded as the invention is particularly pointed out and distinctly claimed in the claims at the conclusion of the specification. The foregoing and other features, and advantages of the invention will be readily understood from the following detailed description of preferred embodiments taken in conjunction with the accompanying drawings in which:

DETAILED DESCRIPTION

In accordance with the principles of the present invention, systems and methods for freezing, thawing and storing biopharmaceutical materials are provided.

Figure 1:
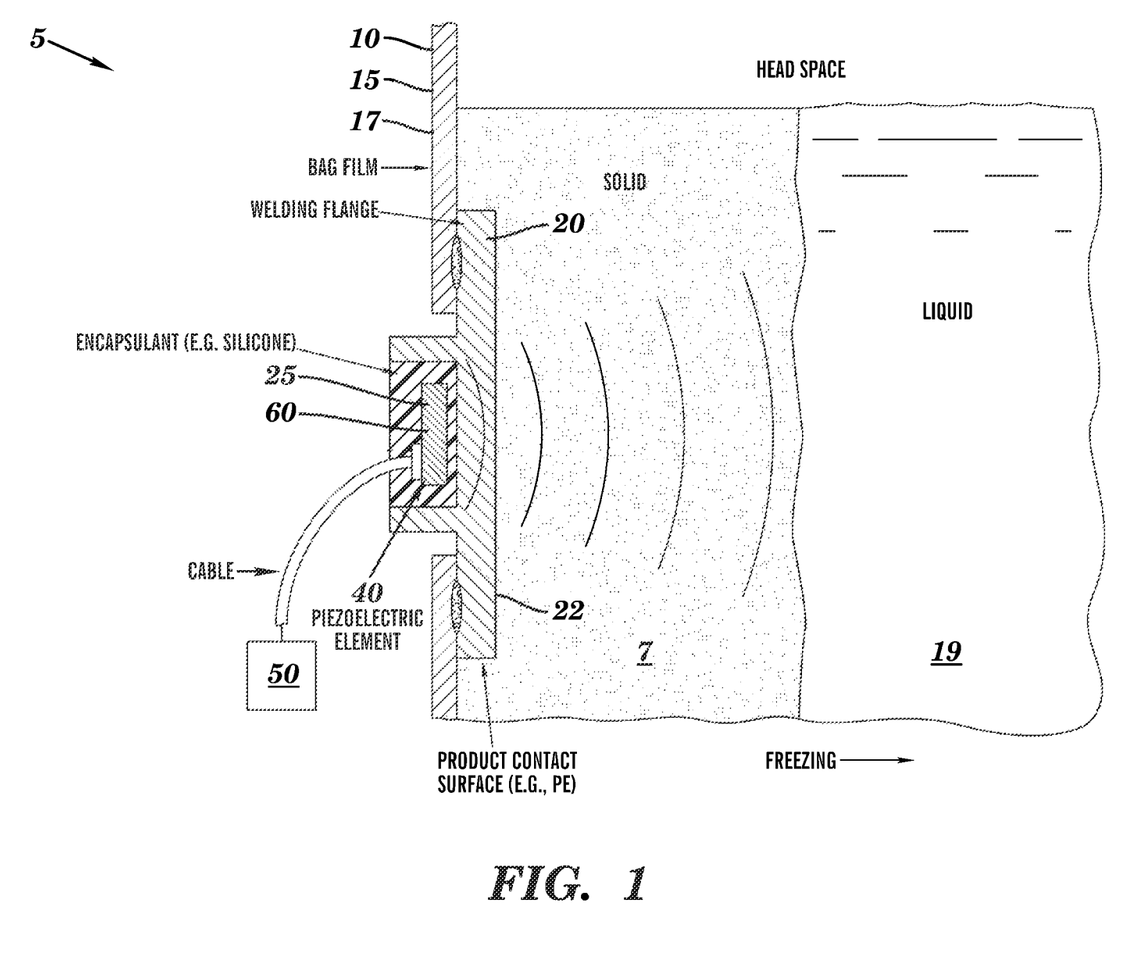
FIG. 1 is a side cross-sectional view of a system for use in freezing or thawing biopharmaceutical materials in accordance with the present invention.

In an exemplary embodiment depicted in FIG. 1, a system 5 for cooling, freezing, preserving, processing and thawing biopharmaceutical materials 7, such as bulk drug substance, is shown. The system may include a sterile container, such as a flexible container 10 formed of polyethylene and configured to contain the bulk drug substance. A support member 20 may be connected to and supported by container 10.

As depicted in FIG. 1, a film 15 forming container 10 may have a sidewall 17 to which support member 20 is connected via an ultrasonic welding technique, or other means of mounting support member 20, such that support member 20 is supported by container 10 and such that the biopharmaceutical material in an interior 19 of container 10 is substantially sealed inside container 10 (i.e., sealed such that the biopharmaceutical materials are prevented or inhibited from leaking out of container 10). Support member 20 may have a cavity 25 receiving a transmitter and/or sensor for sending and receiving ultrasonic pulses toward the biopharmaceutical material held in interior 19. For example, an ultrasonic sensor 40 (e.g., a piezoelectric transducer) may convert electrical energy into high frequency acoustic energy and vice-versa to perform the function of both the transmitter and receiver. A controller 50 may be coupled to sensor 40 such that controller 50 may control the transmission of ultrasonic waves by sensor 40 and may interpret or analyze signals received by sensor 40.

In operation, an ultrasonic sensor (e.g., sensor 40) is placed in contact with, or is acoustically coupled to, a biopharmaceutical material to be tested. An electronics package (e.g., controller 50) emits an electrical pulse along a cable connected to the sensor. The sensor converts the electrical pulse into an acoustic pulse which is then propagated into the test material. If the acoustic pulse encounters an interface between two different materials, such as a phase change of a material, some portion of the acoustic energy is reflected back toward the sensor, where it is converted into electrical energy and interpreted by a controller coupled to the sensor. In particular, the reflected signal, or echo, is detected by the electronics package (e.g., controller 50) and analyzed to determine the distance between the sensor and the interface. This distance to the interface may allow further analysis relative to the degree to which the biopharmaceutical material is frozen or thawed.

As depicted in FIG. 1, cavity 25 may be filled with an encapsulant 60 (e.g., silicone) which may acoustically couple sensor 40 to biopharmaceutical material 7 held in container 10. Encapsulant 60 substantially fills cavity 25 such that no air gap is present in cavity 25 to inhibit the loss of acoustic signal as an ultrasonic pulse transmitted by sensor 40 travels from sensor 40 through encapsulant 60 through sidewall 17 into biopharmaceutical material 7. The presence of such an air gap would result in the loss of any signal (e.g., an ultrasonic pulse transmitted by sensor 40) passing through such an air gap. Thus, as described cavity 25 is substantially filled with the encapsulant to provide such an acoustical coupling.

As depicted in FIG. 1, support member 20 and sensor 40 may be located on sidewall 17 such that an inner surface 22 of support member 20 contacts a solid or frozen portion of biopharmaceutical material 7 and the acoustic signal is transmitted from sensor 40 substantially parallel to a direction of ice growth depicted by the arrow in FIG. 1. As depicted, the biopharmaceutical material includes a liquid portion and a solid portion, which would allow a determination of a location of a phase change as described. Further, a headspace may be located above the solid and liquid portions.

Figure 2:
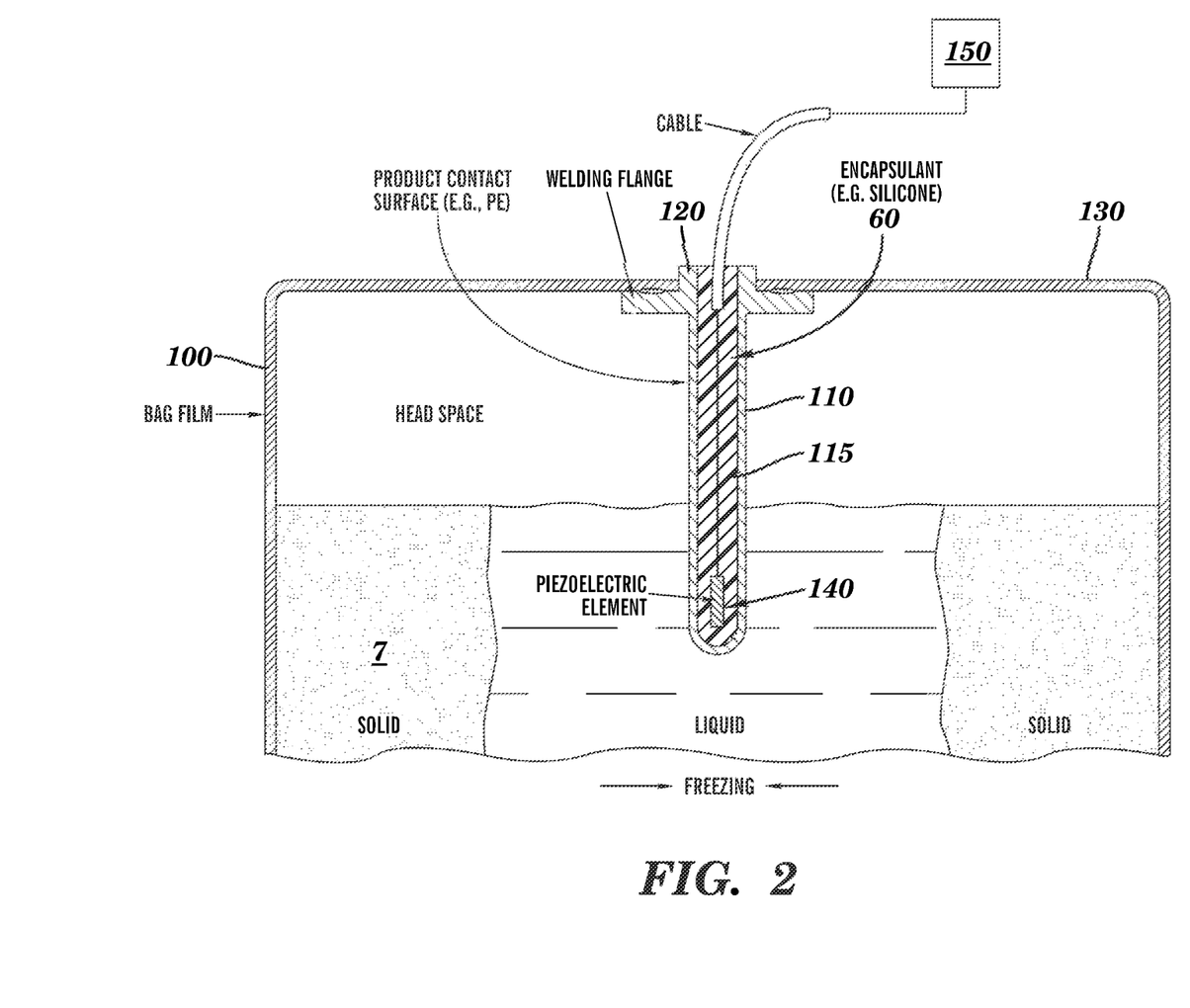
FIG. 2 is a side cross-sectional view of another embodiment of a system for freezing or thawing biopharmaceutical materials in accordance with the present invention.

In another example depicted in FIG. 2, an ultrasonic sensor 140 may be located in a support member 120 connected to a container, for example, a top side 130 of a container 100 holding biopharmaceutical material 7 such that a probe portion 110 of support member 120 extends downwardly into biopharmaceutical material 7 below an interface between a headspace and a liquid portion of the biopharmaceutical material and laterally between one or more frozen portions thereof. Support member 120 may be welded to top side 130 of container 100 to substantially seal the biopharmaceutical material therein and inhibit leakage thereof as described above relative to container 10. Encapsulant 60 may fill a cavity 115 of support member 120 similar to cavity 25 described above to acoustically couple sensor 140 to the biopharmaceutical material via the encapsulant and probe portion 110. As described above relative to sensor 40, sensor 140 may transmit an ultrasonic pulse which may be reflected by a phase change between liquid and solid biopharmaceutical materials such that the reflection may be received by the sensor and analyzed by a controller 150 coupled to sensor 140 to determine a phase change location. The pulse may be transmitted vertically or perpendicular to a direction of ice growth depicted by the arrows in FIG. 2.

Figure 3:
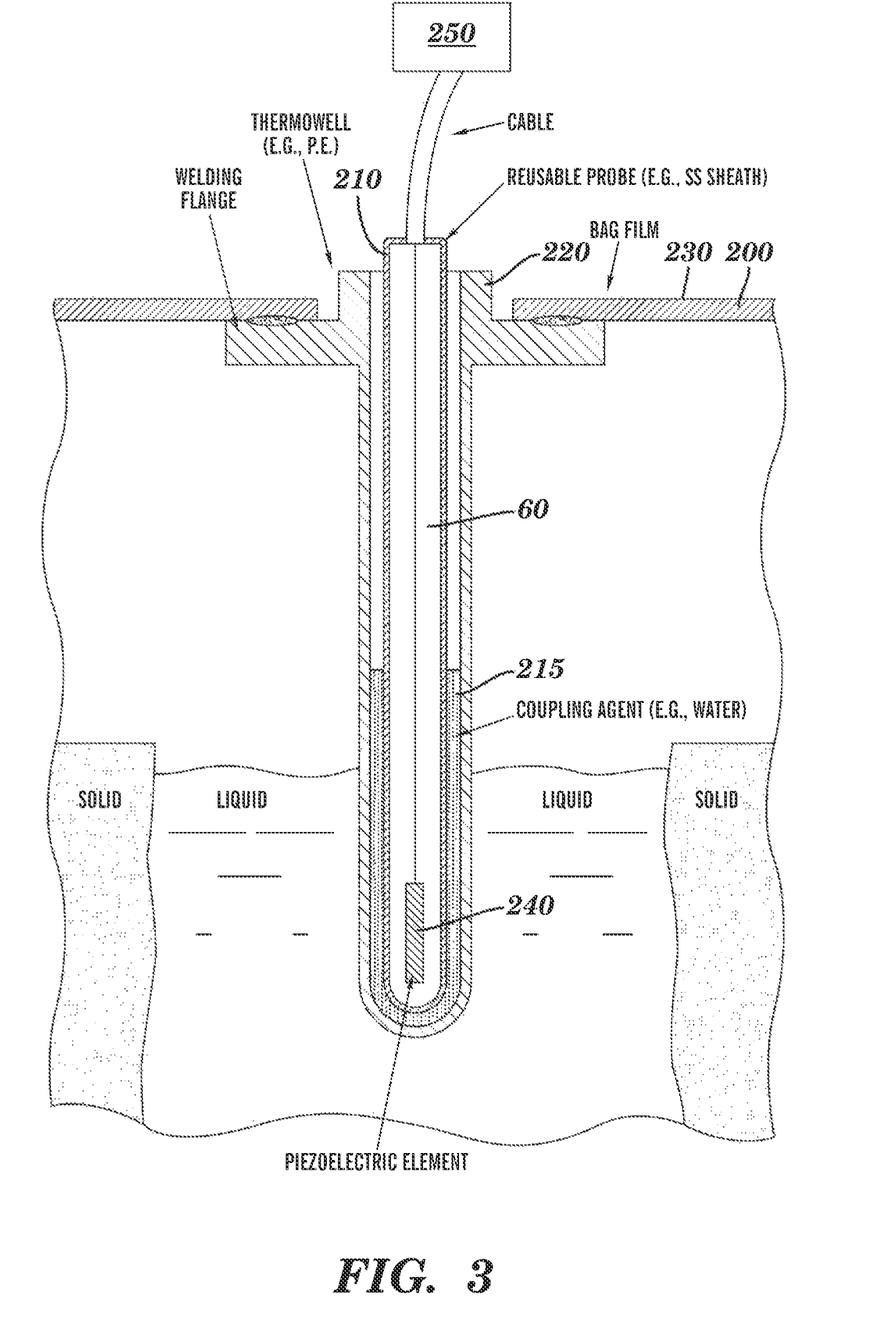
FIG. 3 is a side cross-sectional view of a further embodiment of a system for freezing or thawing biopharmaceutical materials in accordance with the present invention.

In a further example depicted in FIG. 3, an ultrasonic sensor 240 may be removably located in a sensor well 220 connected to a container and, for example, a top side 230 of a container 200 holding biopharmaceutical material 7. Sensor well 220 may be a device which provides isolation of a sensor from the media (e.g., biopharmaceutical materials) being sensed. The media may be a solid, liquid or gas and the isolation may provide protection, sterility and/or removability of a sensor placed therein. Sensor 240 may be part of a probe 210 received in sensor well 220 such that probe 210 extends downwardly within sensor well 220 into biopharmaceutical material 7 below an interface between a headspace and a liquid portion of the biopharmaceutical material. Sensor well 220 may be welded to top side 230 of container 200 such that the connection is substantially sealed and the biopharmaceutical material does not enter sensor well 220. Probe 210 may be inserted into sensor well 220 prior to a measurement of a phase change of biopharmaceutical material 7 being taken by sensor 240 coupled to a controller 250, and probe 210 may be removed from sensor well 200 once the measurement is completed or as desired. A user may fill a cavity 215 of sensor well 220 with water or another liquid to provide an acoustical coupling between sensor 240 and the biopharmaceutical material via sensor well 220 prior to the biopharmaceutical material being tested. Sensor 240 may be directly connected to an interior surface of probe 210 to acoustically couple sensor 240 to probe 210 and thus the water in cavity 215, sensor well 220 and the biopharmaceutical material. In another example, probe 210 could include an encapsulant or other coupling agent (e.g. encapsulant 60) in an interior portion thereof to couple sensor 240 to such an interior surface of probe 210 to acoustically couple sensor 240 to the water or other coupling agent in cavity 215, sensor well 220 and the biopharmaceutical material. As described above relative to sensor 40 and sensor 140, sensor 240 may transmit an ultrasonic pulse which may be reflected by a phase change between liquid and solid biopharmaceutical materials such that the reflection may be received by the sensor and analyzed by controller 250 coupled to sensor 240.

Figure 4:
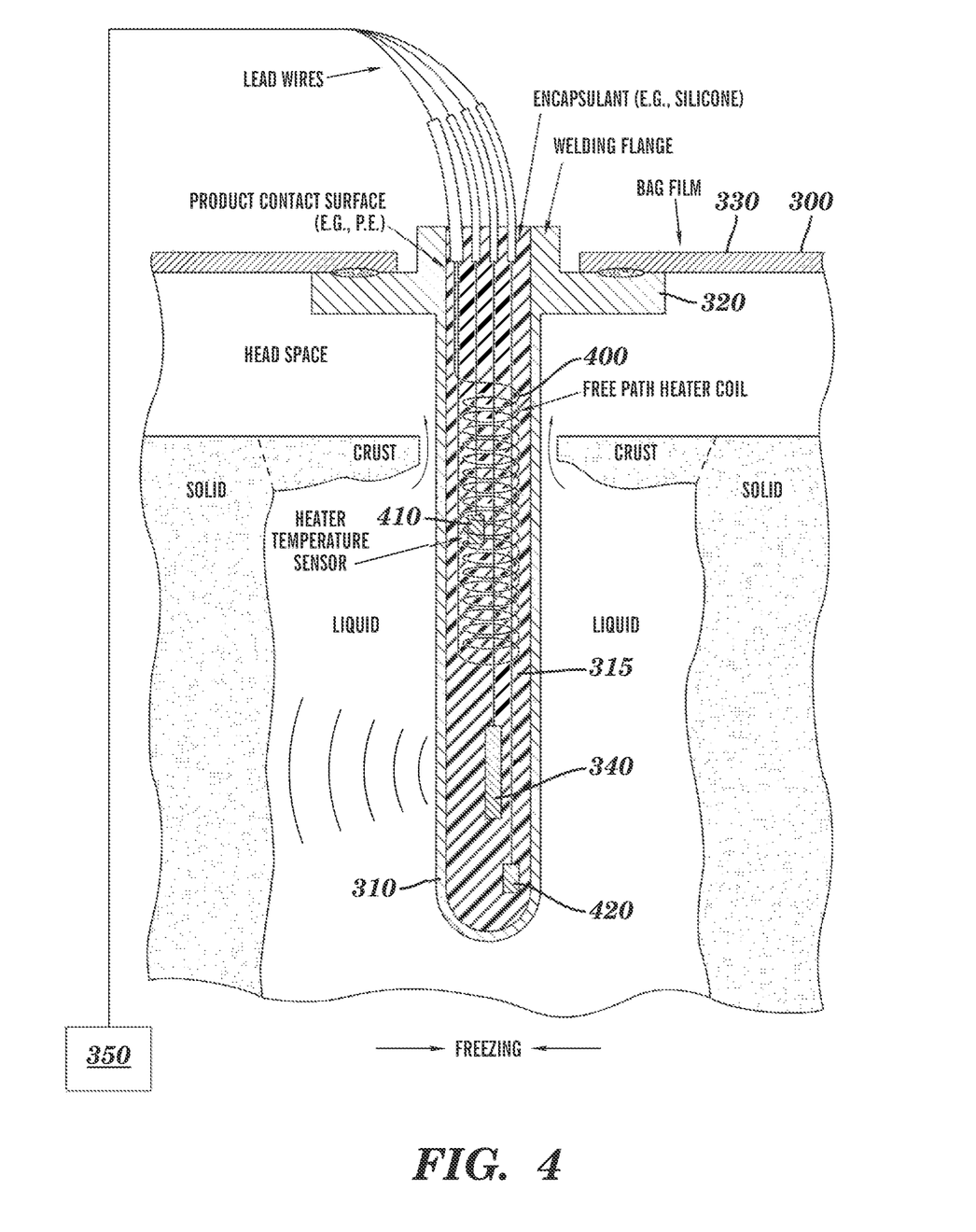
FIG. 4 is a side cross-sectional view of yet a further embodiment of a system for freezing or thawing biopharmaceutical materials in accordance with the present invention.

In yet a further example depicted in FIG. 4, an ultrasonic sensor 340 may be located in a probe portion 310 of a support member 320 connected to a top side 330 of a container, for example, a container 300 holding biopharmaceutical material 7, as described above relative to support member 120 and downwardly depending probe portion 110. Support member 320 may also receive other instruments to enhance the freezing and/or thawing of a biopharmaceutical material held in a container 300. For example, a free-channel heater 400 formed as a coil and a heater temperature sensor 410 may be utilized to direct the expansion of the biopharmaceutical material during freezing. In particular, the heater may ensure that occluded water is always directed into the head space of the container, rather than forcing its way out horizontally, by maintaining an upward path for such water through selective heating of the area immediately around such a heater. The heater may interfere with a product temperature sensor 420 also received in probe portion 320. To inhibit such interference, heater 400 and sensor 420 may be isolated by separating them within the probe or by repeating the following sequence:

1. Heater on for X seconds
2. Heater off for Y seconds
3. Measure product temperature The heater and sensors may be coupled to a controller 350 such that controller 35 may utilize information from the temperature sensors (i.e., heater temperature sensor 410, product temperature sensor 420) and sensor 340 to determine if a process (e.g., freezing or thawing) has been completed. Further, probe portion 310 of support member 320 may extend downwardly into biopharmaceutical material 7 in container 300 below an interface between a headspace and a liquid portion of the biopharmaceutical material as depicted in FIG. 4. Support member 320 may be welded to top side 330 of container 300 to connect and substantially seal support member 320 relative to container 200. Encapsulant 60 may fill a cavity 315 of support member 320 (similar to cavity 25 and cavity 115 described above) to acoustically couple sensor 340 to the biopharmaceutical material. As described above relative to sensor 40 and sensor 140, sensor 340 may transmit an ultrasonic pulse which may be reflected by a phase change between liquid and solid biopharmaceutical materials such that the reflection may be received by the sensor and interpreted by a controller 350 coupled to the sensor. In another unillustrated example, a removable probe having a sensor therein, similar to probe 210, may receive other instruments (e.g., heater and temperature sensors) to enhance the freezing and/or thawing of biopharmaceutical materials held in a container as described above relative to probe portion 310 of support member 320.

In a further example, multiple ultrasonic sensors (e.g., sensor 40, 140, 240, 340) may be utilized to determine multiple locations (e.g., of phase changes) within biopharmaceutical materials held in a container (e.g., container 10, container 100, container 200, container 300) and therefore further characterize the degree of phase change of the biopharmaceutical material. For example, complex arrangements may be created using multiple transducers (e.g., ultrasonic sensors) in a phased array arrangement. In a phased array, the electronics package (e.g., controller 50) staggers the timing of the electrical pulse sent to each transducer such that the transmission of ultrasonic pulses to the material to be tested is correspondingly staggered. Depending on the timing, the resulting acoustic wavefront emitted by the sensor may be steered to obtain a more complete picture of the material being tested. In addition, the use of multiple transducers can provide improved spatial resolution.

Further, the described ultrasonic sensors may include transmitters and receivers housed integrally together in a single housing (e.g., a piezoelectric element) as described above, or such transmitters and receivers could be separate from one another and housed separately from each other about a material (e.g., biopharmaceutical material) to be tested. Such sensors and/or receivers may be mounted in multiple support members connected to a container in various locations holding such a material (e.g., biopharmaceutical material) such that the support members are sealed relative to the container. Further, the support member could be sealed relative to an interior of the container or could be open allowing contact between the biopharmaceutical material and the sensor(s) and/or encapsulant.

Also, as described above, it is desirable that any spaces or gaps be minimized between the ultrasonic sensors (e.g., sensor 40, sensor 140, sensor 240 and sensor 340) and any object (e.g., biopharmaceutical material) to which it is desired to acoustically couple the sensor to. Also, the controllers (e.g., controller 50, controller 150, controller 250 and controller 350) may be a pulse transmitter/receiver as known by those skilled in the art, including, for example, an Olympus NTD model number 5077PR having an ultrasonic band and square wave. The sensors (e.g., sensor 40, sensor 140, sensor 240, and sensor 340) described above coupled to the controllers may be combined transmitters/receivers having, for example, a central frequency of 2.5 megahertz (MHz). Such sensors may be located in a plastic housing. The controllers may receive a return signal from the sensor and output it to an oscilloscope (e.g., an AGILENT DS 07012A digital oscilloscope) for further analysis. Also, additional signal processing may be performed on a personal computer connected to such an oscilliscope. Such processing may include calibration, calculation of distance to a liquid/solid interface, calculation of the degree to which a bulk of substance is frozen or thawed, and a calculation of a temperature of such biopharmaceutical material.

The containers described above (e.g., container 10, container 100, container 200, and container 300) may be formed of a laminated film which includes a plurality of layers. Also a biocompatible product-contacting layer of the interior of the containers may be formed of a low density polyethylene, very low density polyethylene, ethylene vinyl acetate copolymer, polyester, polyamide, polyvinylchloride, polypropylene, polyfluoroethylene, polyvinylidenefluoride, polyurethane or fluoroethylenepropylene, for example. A gas and water vapor barrier layer may also be formed of an ethylene/vinyl alcohol copolymer mixture within a polyamide or an ethylene vinyl acetate copolymer. Further, the containers may include a layer with high mechanical strength (e.g. a polyamide), and an external layer with insulating effect to heat welding, for example, polyester. The layers may be compatible with warm and cold conditions and may be able to withstand ionizing and gamma irradiation for sterilization purposes. Further, the processes (e.g., monitoring of freezing and thawing of biopharmaceutical materials) described above may be utilized with reusable containers, such as Sartorius Stedim Biotech's CRYOVESSEL, a stainless steel freeze-thaw vessel.

The containers described above may be adapted to receive and contain frozen and/or liquid biopharmaceutical materials. In an embodiment, the biopharmaceutical materials described herein could include bulk drug substance, protein solutions, protein formulations, amino acid solutions, amino acid formulations, peptide solutions, peptide formulations, DNA solutions, DNA formulations, RNA solutions, RNA formulations, nucleic acid solutions, nucleic acid formulations, antibodies and their fragments, enzymes and their fragments, vaccines, viruses and their fragments, biological cell suspensions, biological cell fragment suspensions (including cell organelles, nuclei, inclusion bodies, membrane proteins, and/or membranes), tissue fragments suspensions, cell aggregates suspensions, biological tissues in solution, organs in solution, embryos in solution, cell growth media, serum, biologicals, blood products, preservation solutions, fermentation broths, and cell culture fluids with and without cells, mixtures of the above and biocatalysts and their fragments.

Further, only a portion of each of the containers (e.g., container 10, container 100, container 200, and container 300) are depicted in the figures included herein. Such containers could be in any desirable shape for storing or transporting such containers. As indicated, multiple ultrasonic transmitters and sensors may be utilized in such containers to determine a phase change of solutions (e.g., biopharmaceutical materials) held in such containers.

As indicated above, a controller (e.g., controller 50, controller 150, controller 250, controller 350) may determine a phase change of an aqueous solution (e.g., biopharmaceutical materials) based on an analysis of a propagation and echo of an ultrasonic pulse sent to such an aqueous solution. For example, a distance of a phase change may be determined by multiplying an echo delay by the speed of sound in a particular medium (e.g., water). Such a determination of a phase change location may further be refined by taking into account different materials of the container, aqueous solution, and a temperature dependence of the speed of sound in water and/or other materials.

While the invention has been depicted and described in detail herein, it will be apparent to those skilled in the relevant art that various modifications, additions, substitutions and the like can be made without departing from the spirit of the invention and these are therefore considered to be within the scope of the invention as defined in the following claims.

The invention claimed is:

1. A system for use in freezing or thawing a biopharmaceutical material, said system comprising;
   a container means having a receiving cavity for receiving a biopharmaceutical material therein;
   a support member connected to and supported by said container means;
   a transmitter configured to propagate an ultrasonic pulse into said biopharmaceutical material, said transmitter located in a support member cavity of said support member, said support member cavity bounded by a plurality of walls of said support member;
   an exterior wall of said plurality of walls bounding said receiving cavity, said support member cavity comprising a coupling agent therein;
   an ultrasonic sensor configured to sense a reflection of said pulse in said biopharmaceutical material, said sensor located in said support member cavity, said coupling agent located between said sensor and said exterior wall to acoustically couple said sensor to said receiving cavity and the biopharmaceutical material; and
   a controller coupled to said transmitter and said sensor, said controller configured to determine a phase change of said biopharmaceutical material based on said propagation of said pulse by said transmitter and said sense of said reflection by said sensor; and
   wherein said support member cavity comprises a sensor well and said transmitter comprises a probe located in said sensor well such that an end of said probe extends into a portion of said sensor well surrounded by a liquid portion of said biopharmaceutical material.

2. The system of claim 1 wherein said transmitter and said sensor consist of a single piezoelectric transducer.

3. The system of claim 1 wherein said transmitter is located such that said pulse is propagated from said transmitter through a solid phase of said biopharmaceutical material substantially parallel to a direction of ice growth of said biopharmaceutical material and said pulse is reflected at a liquid/solid interface of said biopharmaceutical material.

4. The system of claim 1 wherein said transmitter is located such that said pulse is propagated from said transmitter through a liquid phase of said biopharmaceutical material substantially perpendicular to a direction of ice growth of said biopharmaceutical material and said pulse is reflected at a liquid/solid interface of said biopharmaceutical material.

5. The system of claim 1 wherein said support member cavity avoids communication with an area external to said support member cavity.

6. The system of claim 1 wherein said sensor is removably received in said support member cavity.

7. The system of claim 1 wherein said support member cavity comprises a heater configured to heat the biopharmaceutical material to provide a pathway for a liquid portion of the biopharmaceutical material toward a head space above the biopharmaceutical material.

8. The system of claim 1 wherein said support member cavity comprises an encapsulant substantially filling an empty portion of said support member cavity between said sensor and an interior wall of said support member adjacent said biopharmaceutical material and bounding said support member cavity to acoustically couple said sensor to said biopharmaceutical material.

9. The system of claim 8 wherein said support member is fixedly connected to said container means such that an exterior surface of said support member contacts said biopharmaceutical material.

10. The system of claim 1 wherein said support member cavity has an end in communication with an area external to said support member cavity to allow said sensor to be removably inserted into said support member cavity.

11. The system of claim 10 wherein said support member cavity receives a coupling agent between said sensor and an interior wall of said support member adjacent said biopharmaceutical material and bounding said support member cavity to acoustically couple said sensor to said biopharmaceutical material.

12. A method for use in freezing or thawing a biopharmaceutical material, the method comprising:
receiving a biopharmaceutical material in a receiving cavity of a container means, said container means being connected to and supporting a support member; propagating an ultrasonic pulse via a transmitter into the biopharmaceutical material, the transmitter located in a support member cavity of the support member, the support member cavity bounded by a plurality of walls of the support member;
an exterior wall of the plurality of walls bounding the receiving cavity, the support member cavity comprising a coupling agent therein; sensing a reflection of the pulse in the biopharmaceutical material using an ultrasonic sensor located in the support member cavity;
the coupling agent located between the sensor and the exterior wall and acoustically coupling the sensor to the receiving cavity and the biopharmaceutical material;
the support member cavity comprising a sensor well and the transmitter comprising a probe located in the sensor well such that an end of the probe extends into a portion of the sensor well surrounded by a liquid portion of the biopharmaceutical material; and
determining a phase change of the biopharmaceutical material based on the propagation of the pulse by the transmitter and the sense of reflection by the sensor using a controller coupled to the transmitter.

13. The method of claim 12 wherein the transmitter and the sensor consist of a single piezoelectric transducer.

14. The method of claim 12 further comprising mounting a support member on a sidewall of the container means.

15. The method of claim 12 further comprising mounting a support member on a top wall of the container means.

16. The method of claim 12 further comprising avoiding communication between the support member cavity and an area external to the support member cavity.

17. The method of claim 12 further comprising removably receiving the sensor in the support member cavity.

18. The method of claim 12 further comprising providing communication between an end of the support member cavity and an area external to the support member cavity to allow the sensor to be removably inserted into the support member cavity.

19. The method of claim 12 further comprising introducing an encapsulant into the support member cavity to substantially fill an empty portion of the support member cavity between the sensor and an interior wall of the support member adjacent the biopharmaceutical material and bounding the support member cavity to acoustically couple the sensor to the biopharmaceutical material.

20. The method of claim 19 further comprising fixedly connecting the support member to the container means such that an exterior surface of the support member contacts the biopharmaceutical material.

21. A system for use in freezing or thawing a biopharmaceutical material, said system comprising:
a container means having a receiving cavity for receiving a biopharmaceutical material therein;
a support member connected to and supported by said container means, said support member fixedly connected to said container means such that an exterior surface of said support member contacts said biopharmaceutical material;
a transmitter configured to propagate an ultrasonic pulse into said biopharmaceutical material, said transmitter located in a support member cavity of said support member, said support member cavity bounded by a plurality of walls of said support member;
an exterior wall of said plurality of walls bounding said receiving cavity, said support member cavity comprising a coupling agent therein;
an ultrasonic sensor configured to sense a reflection of said pulse in said biopharmaceutical material, said sensor located in said support member cavity, said coupling agent located between said sensor and said exterior wall to acoustically couple said sensor to said receiving cavity and the biopharmaceutical material; and
a controller coupled to said transmitter and said sensor, said controller configured to determine a phase change of said biopharmaceutical material based on said propagation of said pulse by said transmitter and said sense of said reflection by said sensor.

22. The system of claim 21 wherein said support member cavity comprises a sensor well and said transmitter comprises a probe located in said sensor well such that an end of said probe extends into a portion of said sensor well surrounded by a liquid portion of said biopharmaceutical material.

23. A method for use in freezing or thawing a biopharmaceutical material, the method comprising:
receiving a biopharmaceutical material in a receiving cavity of a container means, said container means being connected to and supporting a support member;
fixedly connecting the support member to the container means such that an exterior surface of the support member contacts the biopharmaceutical material;
propagating an ultrasonic pulse via a transmitter into the biopharmaceutical material, the transmitter located in a support member cavity of the support member, the support member cavity bounded by a plurality of walls of the support member;
an exterior wall of the plurality of walls bounding the receiving cavity, the support member cavity comprising a coupling agent therein; sensing a reflection of the pulse in the biopharmaceutical material using an ultrasonic sensor located in the support member cavity;
the coupling agent located between the sensor and the exterior wall and acoustically coupling the sensor to the receiving cavity and the biopharmaceutical material; and
determining a phase change of the biopharmaceutical material based on the propagation of the pulse by the transmitter and the sense of reflection by the sensor using a controller coupled to the transmitter.

24. The method of claim 23 wherein the support member cavity comprises a sensor well and the transmitter comprises a probe located in the sensor well such that an end of the probe extends into a portion of the sensor well surrounded by a liquid portion of the biopharmaceutical material.

* * * * *